(12) United States Patent
Zhu et al.

(10) Patent No.: US 7,807,216 B2
(45) Date of Patent: Oct. 5, 2010

(54) PROCESS FOR PRODUCING NANOCRYSTALLINE COMPOSITES

(75) Inventors: Weiguang Zhu, Singapore (SG); Zhihong Wang, Singapore (SG); Ooi Kiang Tan, Singapore (SG); Changlei Zhao, Singapore (SG)

(73) Assignee: Nanyang Technological University, Nanyang Avenue (SG)

( * ) Notice: Subject to any disclaimer, the term of this patent is extended or adjusted under 35 U.S.C. 154(b) by 1393 days.

(21) Appl. No.: 10/516,059

(22) PCT Filed: May 16, 2003

(86) PCT No.: PCT/SG03/00116

§ 371 (c)(1),
(2), (4) Date: May 31, 2005

(87) PCT Pub. No.: WO03/099741

PCT Pub. Date: Dec. 4, 2003

(65) Prior Publication Data

US 2005/0255239 A1    Nov. 17, 2005

(30) Foreign Application Priority Data

May 24, 2002    (SG)    ............................. 200203154-0

(51) Int. Cl.
| B05D 5/12 | (2006.01) |
| B05D 3/02 | (2006.01) |
| H01L 41/22 | (2006.01) |
| H04R 17/00 | (2006.01) |

(52) U.S. Cl. .................... 427/100; 427/372.2; 29/25.35; 347/68

(58) Field of Classification Search ................. 427/100, 427/372.2
See application file for complete search history.

(56) References Cited

U.S. PATENT DOCUMENTS

| 5,500,988 | A | * | 3/1996 | Moynihan et al. .......... 29/25.35 |
| 6,230,378 | B1 | * | 5/2001 | Cramer et al. ............. 29/25.35 |
| 6,247,799 | B1 | * | 6/2001 | Sakamaki et al. ............. 347/68 |
| 6,355,185 | B1 | * | 3/2002 | Kubota .................. 252/62.9 R |
| 6,432,238 | B1 | * | 8/2002 | Yun et al. ................. 156/89.12 |

* cited by examiner

*Primary Examiner*—Timothy H Meeks
*Assistant Examiner*—Cachet I Sellman
(74) *Attorney, Agent, or Firm*—Blakely Sokoloff Taylor & Zafman LLP

(57) ABSTRACT

A process to produce dense nanocrystalline composites such as ceramic bodies, coatings and multi-layered devices with uniform microstructure is disclosed. The invention utilizes sol-gel solutions to reduce agglomeration of nanocrystalline powders in the production of "green bodies" or intermediate products. This novel use of sol-gel solutions also reduces grain growth and porosity in products during sintering. In finished products, final grain sizes are typically less than 100 nm with densities of the final products approaching 99.5% of theoretical densities. In addition, sintering temperatures required are lower than those in conventional methods, typically less than 1,100° C. While FIG. 1 shows one application of this novel process, this invention has wide application in the manufacture of many other products, particularly for composite coatings and in the production of nanodevices.

9 Claims, 1 Drawing Sheet

PROCESS FOR PRODUCING NANOCRYSTALLINE COMPOSITES

CROSS REFERENCE TO RELATED APPLICATIONS

The present patent application is a non-provisional application of International Application No. PCT/SG03/00116, filed May 16, 2003.

FIELD OF THE INVENTION

The present invention relates in general to producing nanocrystalline composites, including ceramic bodies, coatings and multi-layered products, and more particularly, to producing nanocrystalline composites by dispersing nanocrystalline particles into a related organo-metallic precursor solution to produce nanocrystalline composites.

BACKGROUND OF THE RELATED ART

"Nanocrystalline" or "nanosized" particles are hereinafter to be understood to mean particles, the average size of which is not more than 100 nanometers (nm) in diameter and particularly preferably not more than 30 nm in diameter. "Organo-metallic precursors" are used as carrier media, and which can include dispersion aids for ensuring that the particles are uniformly dispersed in a medium.

"Nanocrystalline composites", in the present invention, refer predominantly to bulk materials or coatings which contain at least one phase of materials and in which the grains of all phases are less than 100 nm, either in starting materials known as "green bodies" or in final products such as coatings, ceramics or composites.

The first step in the production of a nanocrystalline particle or nanoparticle to a fully dense composite is the compaction of powder comprising of nanocrystalline particles to form a "green body", which is an intermediate product. This is conventionally done by using an uni-axial press.

Decades of research on conventional ceramic processing have shown that the uniformity and density of particle packing in the green body has a significant influence on how well the green body will densify and consequently on how large the sizes of grains will develop to during sintering. Conventional nanocrystalline particles, however, are at a disadvantage in this regard.

There are essentially two problems encountered, namely the agglomeration of particles in the processing of these nanocrystalline particles and the difficulty of producing of ceramic green bodies with high solid content or high green density.

The first problem, agglomeration of particles in the nanometer range, is common because of inter-particle London-van der Waals forces and functional groups on the particle surface. Most nanocrystalline particles currently made are not composed simply of individual single crystals or nanometer-sized particles, known as "crystallites". Crystallites made by conventional methods tend to bond and form larger units termed "agglomerates" or "aggregates".

Thus, the true particle size in most powders is the agglomerate or aggregate size. The presence of either agglomerates or aggregates is extremely deleterious during the sintering of nanocrystalline particles into a solid with grain sizes less than 100 nm. As a rule of thumb, in pressureless sintering of the prior art, it is difficult to obtain a grain size which is less than the starting agglomerate size. Indeed, early attempts at pressureless sintering nanocrystalline ceramics to full density never succeeded in producing less than 100 nm grain sizes. Typically, grain sizes in the order of a micrometer were produced. In large part, this was because samples were fabricated from agglomerated powders. A disadvantage of the prior art is the agglomeration of nanocrystalline particles.

Another problem in the prior art is the low density of green bodies due to high porosity within the green bodies. In conventional methods, nanocrystalline particles are compressed to form "powder compacts". These powder compacts, before they are heated, are composed of individual crystallite or agglomerate separated by between 25 and 60 vol % of porosity, depending on the particular material and processing method used. To improve properties such as strength, translucency and so on, in the final product, it is desirable to reduce as much of this porosity as possible. It is evident that the more homogeneous the particle packing is and the higher solid content a green body has, the easier it will be to get a uniform and dense microstructure during sintering. However these are hard to achieve with conventional techniques.

Nanocrystalline particles, however, have poor compaction behavior compared to conventional sub-micron particles. This can, in many cases, be attributed to the agglomeration present in the starting powders. The compaction of fractal-like agglomerates produces an inhomogeneous particle packing structure within the green body. Even if the agglomerates themselves are extremely dense, large inter-agglomerate pores may lead to poor density in the green body. There are also other difficulties with the compaction of nanocrystalline particles which cannot be attributed to agglomerations.

One known difficulty is the large number of particle-particle point contacts per unit volume in nanocrystalline particles. Each of these point contacts represents a source of frictional resistance to the compaction of the powder and this inhibits particle-particle sliding and particle rearrangement. It is therefore desirable to provide a method with which the nanocrystalline particles can slide against one another and rearrange themselves easily so as to produce a more homogeneously packed green body with relatively high density.

Another problem in conventional methods is the inability to retain an ultra-fine grain size in the product after sintering. Major obstacles include the strong tendency of nanocrystalline particles to agglomerate and the ever-present obstacle of unwanted grain growth during sintering. This is because the capillary driving force for sintering (involving surfaces) and grain growth (involving grain boundaries) are comparable in magnitude, both being proportional to the reciprocal grain size. This means that the final-stage sintering processes are inevitably accompanied by the rapid grain growth.

Thus it is now generally recognized that unless this grain growth problem can be overcome, the conventional pressureless sintering process cannot produce dense ceramics with nanometer-scale structure (grain size less than 100 nm), leading many researchers to resort to the approach of high-pressure consolidation. High pressure results in a marked increase in the number of nucleation events so that the final grain size is small. This is because final grain size is determined by the number of nuclei formed, that is, the number of grains present that can impinge on one another. It is therefore desirable to provide a method to promote the nucleation of primary crystallization and control its uniformity during sintering.

Most recently, a simple two-step sintering method without applied pressure was reported by Chen & Wang (Nature 404: 168-171; 9 Mar. 2000) where fully dense cubic $Y_2O_3$ with a grain size of 60 nm was successfully prepared. That sintering method used a two-step heating schedule. The sample was first heated to a high temperature to achieve an intermediate density, then cooled and held at a lower temperature until it was fully dense. To succeed such a two-step sintering, a sufficient high starting density should be obtained during the first step. When the density is above 70% porosity, data have shown that all pores in $Y_2O_3$ become sub-critical and unstable against shrinkage (which occurs by capillary action). These pores can be filled as long as grain boundary diffusion allows it, even if the particle network is frozen as it clearly is in the second step. It was found that densities higher than 75% were adequate for subsequent second step sintering. This result further emphasizes the importance of the production of green bodies with high solid content in nanocrystalline composite preparation.

Having noted the abovementioned problems of agglomeration and poor uniformity and density, Helmut Schmidt et al, in U.S. Pat. No. 5,590,387, disclosed a method to overcome these problems by modifying nanocrystalline particles with surface modifier and then re-dispersing it in water, an organic solvent or a mixture of both, to form a suspension. However, this improvement itself presented a disadvantage as the surface modifier and organic solvent were entirely removed after burning out, the green body ready for sintering still did not have sufficiently high density.

The present invention seeks to overcome or at least alleviate these problems in the prior art.

OBJECTS OF THE INVENTION

A specific object of the present invention is to provide a method for reducing the agglomeration of the nanocrystalline particles during the process of producing nanocrystalline composites.

Another specific object of the present invention is to provide a method for allowing nanocrystalline particles to slide against one another and rearrange themselves easily during compaction so as to produce a more homogeneously packed green body with a relatively higher density.

Another specific object of the present invention is to provide a method for promoting and controlling the nucleation of primary crystallization so as to produce a more homogeneous microstructure with finer grain size.

Yet another specific object of the present invention is to provide a method for producing denser, thicker sol-gel coatings on metal, glass, ceramic or silicon substrates at relatively lower sintering temperatures.

A more specific object of the present invention is to provide a method for producing nanocrystalline ceramics which incorporates conventional pressureless sintering.

Another more specific object of the present invention is to provide a method for producing denser, thicker piezoelectric films with a more homogeneous microstructure on a substrate.

Yet another more specific object of the present invention is to provide a method for producing multi-layered devices, including capacitors, transformers, resonators, filters and actuators, at very low sintering temperatures.

SUMMARY OF THE INVENTION

A general object of the present invention is to provide a process for producing fully dense nanocrystalline composites, including sintered ceramic bodies, coatings and multi-layered devices, characterized by a nanostructure with a grain size below 100 nm and density up to 99.5% of the theoretical density.

BRIEF DESCRIPTION OF THE FIGURE

The main steps of the present invention is given in the flow chart of FIG. 1.

DETAILED DESCRIPTION OF PREFERRED EMBODIMENTS

Figure 1:
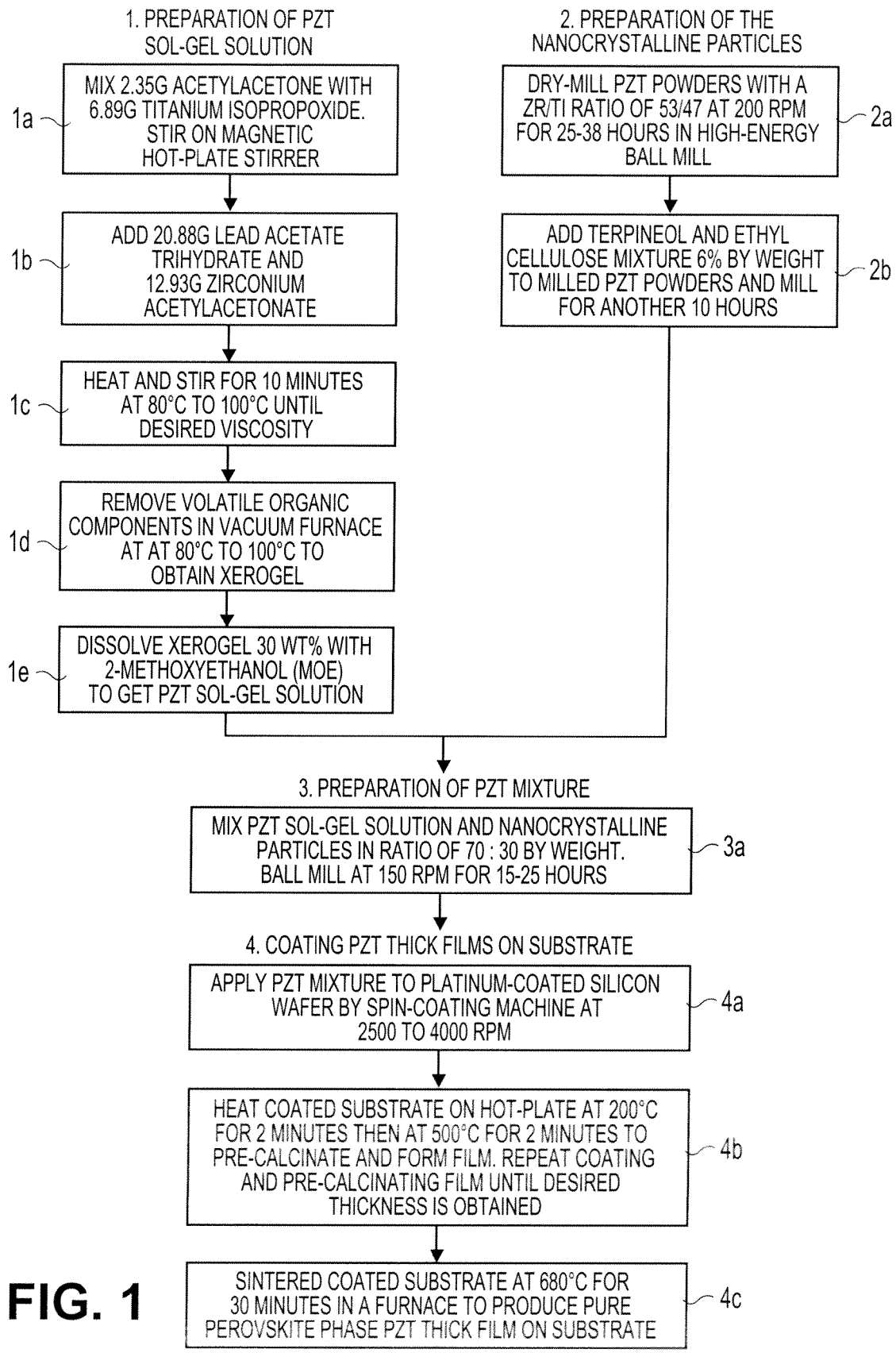

With reference the FIG. 1, a preferred embodiment of the present invention is described and one skilled in the art will be able to reproduce the steps, The method comprises the steps of:

(1) Preparation of PZT Organo-Metallic Solution.

In a typical PZT recipe, 2.35 g of acetylacetone is first mixed in a glass beaker by stirring with 6.89 g titanium isopropoxide on a magnetic hot-plate stirrer to get a stabilized solution.

Then, 20.88 g of lead acetate trihydrate and 12.93 g of zirconium acetylacetonate are added and dissolved in the solution. The solution is heated and stirred to fully dissolve the solids.

The time and temperature are varied (typically 10 minutes at 80° C. to 100° C.) to adjust the viscosity until a clear and sticky solution is obtained. The resulting solution is then further processed under reduced pressure in a vacuum furnace at 80° C. to 100° C. to remove volatile components and a xerogel of $Pb_{1.1}(Zr_{0.53}Ti_{0.47})O_3$ is obtained. Actually, an xerogel with the general formula of $Pb_{1+y}(Zr_xTi_{1-x})O_3$ (where x may be 0 to 1) can be prepared with this method for different applications.

By further dissolving 20 to 40 wt % of the resulting xerogel into 2-methoxyethanol (MOE) in glass beaker on a magnetic stirrer hot-plate, the organo-metallic precursor solution of PZT can be obtained. The xerogel can also be dissolved into alcohol, isopropanel, 2-ethyloxyeathanal, 1,3-propanediol, acetic acid and other similar solutions to get different sol-gel solutions.

(2) Preparation of the Mixture.

PZT powders with a Zr/Ti ratio of 53/47 are dry-milled in a high-energy ball-milling machine at 200 rpm for 25-38 hours to get the particles with diameters ranging from 20-50 nm. While we have used nanocrystalline particles obtained from high-energy ball milling, nanocrystalline particles by other methods and from other sources may also be used.

With the nanocrystalline particles, 2-10% surface modifier by weight, preferably a mixture of terpineol and ethyl cellulose, was added to the bowl of the machine and mixed by further ball milling for 5 to 10 hours to produce the surface-modified nanocrystalline particles.

The PZT sol-gel solution obtained previously was than added to this surface-modified nanocrystalline particles and mixed by further ball milling at 150 rpm for 15 to 25 hours to form a dispersion or slurry.

In a preferred embodiment, 20 to 50 parts by weight, preferably 30, of the surface modified nanocrystalline particle mix was blended and mixed in the bowl of the balling milling machine with an methoxyethanol (MOE) based sol-gel solution 50 to 80 parts by weight, preferably 70 parts by weight, to form a mixture which may be a dispersion, slurry or paste. The MOE-based sol-gel solution contains 20 to 40 w %, preferably 30 w %, of xerogel.

(3) Spin-Coating PZT Thick Films on Platinum-Coated Silicon Substrate.

The uniform dispersion prepared from procedure (2) is directly applied onto a planar substrate, preferably a platinum-coated silicon wafer, by a spin-coating machine at 2500 to 4000 revolutions per minute (rpm).

The coated substrate is then heated on a hot plate at 200° C. for 2 min and 500° C. for 2 min to pre-calcinate it and to form a single film with a thickness of up to 1.5 micron. A thicker film may be achieved by repeating the sequence until the desired thickness is obtained.

The film was than finally sintered at 600° C. to 750° C. in a furnace, preferably at 680° C., for 10 to 60 min, preferably for 30 min, to produce a pure perovskite phase PZT thick film.

The PZT films thus deposited onto silicon wafer may be 1 to 100 μm thick Under field emission scanning electron microscopy, the PZT film appears to have a dense, uniform microstructure. The grain size distribution is narrow and the average grain size ranges from about 50 nm to 1 μm depending on the final sintering temperature. It is difficult to distinguish between grains derived from the sol-gel precursor and those from the original nanocrystalline particles in the homogenous matrix. This is because the grains derived from the sol-gel precursor bonds with the added nanocrystalline particles as it develops. The added nanocystalline particles also "grow up" uniformly during the final sintering stage. The dielectric and piezoelectric properties of these films are comparable to those of bulk PZT ceramics. The thick films produced by this method are of sufficiently high quality to produce piezoelectric micro-actuators for micro-electromechanical systems applications and ultrasonic transducers.

The stated objects of the invention as described above may be generally achieved by introducing the novel steps of:
(a) dispersing selected nanocrystalline ceramic particles, in the presence or the absence of a surface modifier, into a selected organo-metallic sol-gel solution to form a uniform stable dispersion;
(b) processing said dispersion, before or after the volatile organic component in the solution is entirely or partly removed, to form green bodies or coatings; and
(a) heating said green bodies or coatings at a predetermined temperature range to produce dense composites with uniform microstructure, including sintered ceramic bodies and coatings.

Specifically, the present invention provides a method for producing a bulk nanocrystalline ceramic by pressureless sintering technique, which comprises the steps of:
(a) dispersing selected nanocrystalline particles, in the presence or the absence of a surface modifier, into a selected organo-metallic sol-gel solution to form a uniform stable dispersion;
(b) reducing volatile components from said dispersion, preferably by reduced pressure drying or freeze spray drying, to form surface modified nanocrystalline particles;
(c) compacting said nanocrystalline particles by a mold-pressing technique (typically by using an uni-axial press);
(d) calcinating said compaction at a relative lower temperature, compared to conventional techniques, to remove all the organic components followed by cold isostatic pressing it to form a green body with high density; and
(e) firing said green bodies at a certain temperature range to produce dense, nanocrystalline ceramic with uniform microstructure.

The present invention also recites a method for preparing thick ceramic coatings on a substrate, which comprises the steps of:
(a) dispersing selected nanocrystalline ceramic particles, in the presence or the absence of a surface modifier, into a selected organo-metallic sol-gel solution to form a uniform stable dispersion;
(b) applying said stable dispersion to a selected substrate, preferably by spin-coating or dip-coating, so as to coat the substrate with a polycrystalline ceramic layer;
(c) heating said ceramic layer coated substrate at a temperature up to about 650 to 1,100° C. to produce dense, thick ceramic films on said substrate.

Yet the present invention further recites a method for preparing a paste for screen-printing thick films or tape-casting green sheets for multi-layered devices such as actuators, capacitors, resonators filters and transformers. The said method comprises the steps of:
(a) dispersing selected nanocrystalline ceramic powders, in the presence or the absence of a surface modifier, into a selected organo-metallic sol-gel solution to form a uniform stable dispersion;
(b) removing the solvent partially or entirely from the dispersion until a desired solid concentration is reached;
(c) blending said processed dispersion with organic vehicles and additives to form a paste, slip or ink ready for screen-printing, tape-casting, injection molding or any other shaping method.

A primary aspect of the invention is the combination of nanocrystalline particles and a related organo-metallic precursor to produce a dense, nanocrystalline composite. A key phenomenon of the disclosed process is the reactivity of the surface function groups on the crystallite surface with species in sol-gel precursor. This reactivity allows sol-gel thin films to strongly bond to surfaces of the individual crystallites. Upon completion of the reaction, the driving force of agglomeration among the nanocrystalline particles is controlled or reduced.

It is a fact that the surface of the nanocrystalline particles is occupied by functional groups such as hydroxyl groups. Surface hydroxyl groups, for example, are present on the surface of oxide powder particles. Due to the large surface-area-to-volume ratio of nanocrystalline particles, these functional groups lead to the formation of hard agglomerates as a result of condensation reactions taking place between individual particles. On the other hand, these groups can act as centers of interaction for necessary organic processing aids such as dispersion aids, binders and the like.

In addition, the hydroxyl groups readily participate in hydrolysis and condensation reactions of the polymer species in organo-metallic precursors. When nanocrystalline particles are suspended in a sol-gel solution, strong bonds are formed between the sol-gel species and the nanocrystalline particles, preventing condensation reactions between individual particles. As a result, the nanocrystalline particles are uniformly dispersed in the framework of the gels after gel-forming reactions of the precursor are completed. The nanocrystalline particles in the green bodies are not agglomerates but individual crystallites. Furthermore, such suspensions can produce green bodies with extremely homogenous particle packing and superior sintering characteristics than those consolidated in the dry state.

The improved homogeneity results from not only the elimination of the agglomerates but also the greater ease with which the particles can slide against and over one another and rearrange without external pressure in the wet state, as compared with the dry state.

A significant advantage and novel aspect of the present invention is attributed to utilization of nanocrystalline particles in the process. In ordinary compaction of powders, the smaller nanocrystalline particle, the smaller the inter-particle pores. Thus, the pore size and porosity in nanosized particle compaction is much smaller than those utilizing sub-micron powders, giving relatively lower permeability and higher density in the green bodies.

Another advantage of the present invention is attributed to using organo-metallic precursors as binders and dispersion media. In the compacted green body prepared by the mixed suspension, the open pores of the green body are impregnated by the sol-gel solution. After the organic components in the gel framework are removed, the residual inorganic components will fill up some of the inter-particle pores, which further reduces the inter-particle pore size, producing higher green density. Moreover, during low temperature sintering, nucleation can only be initiated in the gel matrix within the inter-particle pores, and the grains stop growing when they impinge the added nanoparticles.

Since the final grain size is limited by impingement of the grains on one another, a homogenous fine grain structure will be produced. As the temperature is further raised during the final stage of sintering, the nanosized pores are reduced, resulting in a denser ceramic product.

Yet another advantage of the present invention is that the nature of the dispersed phase may be varied independently of the type of the sol-gel phase, thereby providing a high degree of flexibility in the custom design of composites for any given application.

Another advantage of the present invention over known production process for ceramic layers is improved homogeneity, finer pore size, in the order of several nanometers, allowing higher green densities, superior sintering characteristics and finer grain microstructure. These advantages are particularly useful in producing multi-layered devices at a low sintering temperature, which permits the use of less expensive internal electrode paste. This advantageously contributes to a sharp reduction in the cost of the final device.

Products and devices that may be fabricated by variations in the processes of the present invention include:
- nanocrystalline bulk ceramics as well as dielectric, ferroelectric or piezoelectric films on optic fiber, silicon wafer and other substrates;
- thick sol-gel ceramic coatings for high temperature wear and corrosion protection;
- thermal barrier coatings;
- bioactive coatings;
- low temperature co-firing multi-layered devices; and
- multi-phase nanocrystalline composites.

The following examples serve to further illustrate some of variations in the example of the preferred embodiment given above. It will be appreciated by one skilled in the art that all the process, materials, chemicals and parameters used may be varied without departing from the scope or spirit of the present invention.

Example (1)

Nanocrystalline PZT Ceramic

Slurries with higher solid content as described above in the Detailed Description of the Preferred Embodiment are heated to 80° C. in a vacuum drying furnace to entirely remove the dispersion medium, methoxyethanol (MOE) from the slurries, after which nanosized PZT particles surface coated with a sol-gel layer are obtained. These particles were then compacted by uniaxial pressing at about 10 to 60 MegaPascals (MPa) to get a powder compact. These powder compacts were then calcinated at 500° C. to remove all the organic components followed by cold isostatic pressing it at 400-500 MPa to produce green bodies with high densities. Green bodies thus obtained were then sintered at a temperature between 650 to 1,100° C., preferably at 800° C.

As a result of this process, the PZT ceramics thus obtained advantageously reached relative densities of over 98% of the theoretical density and had average grain sizes below 100 nm.

Example (2)

Screen-Printing PZT Thick Films on $Au/Al_2O_3$ Substrate

For this procedure, 70% to 90% by weight of said uniform dispersion with medium solid content or nanocrystalline PZT particles surface coated with sol-gel layer as described above is blended with 10% to 30% of commercially available organic vehicle and additives known in the art to produce pastes or inks ready for screen-printing, tape-casting, injection molding or other shaping methods. In a preferred embodiment, paste so produced was printed onto an $Au/Al_2O_3$ substrate by screen-printing and subsequently dried at 110° C. for 15 min. The single layer thickness of said printed layer was between 8 to 20 μm. A thicker film was achieved by repeating the sequence until the desired thickness was obtained. The film was than sintered at 600 to 850° C., preferably at 800° C., for 30 to 60 min to produce a pure perovskite phase PZT thick film. The final sub-micron sized grains were fully developed at 800° C. for 30 min.

Example (3)

PZT Multi-Layered Actuators and Transformers Using Inexpensive Internal Electrode Paste In conventional screen-printing PZT films, sintering temperatures of over 1,100° C. are used. In accordance with the present invention, sintering temperatures of less than 1,100° C. are needed. This allows for the manufacture of low-temperature co-firing devices, for example, multi-layered actuators and transformers using tape-casting or in screen-printing as described in Example (2) above.

In a preferred embodiment, multi-layered actuators were produced using screen-printing. An organic layer, preferably a photoresist film such as AZ1518 film, is first deposited on an alumina substrate using a spin coater to separate the multi-layered actuator from the substrate. The film is spin-coated at 1,000 rpm for 30 seconds, and then baked at 150° C. for 30 min and 350° C. for 60 min to drive off the solvent and to cure the photoresist film on the substrate. Commercially available silver-palladium (Ag/Pd) conductor paste, preferably with Ag/Pd mass ratio of 90/10 to 80/20, was printed with the first stencil patterns on the photoresist film and dried at 150° C. for 5 min. The PZT paste obtained from the procedure described above is deposited on the conductor layer by multiple printing and drying at 150° C. for 10 min after each printing. Then the conductor paste is printed with the second stencil pattern on the top of the PZT layer. The cycle of printing alternating electrode and PZT layers is repeated until the desired multi-layered structure is obtained. These laminated bodies are subsequently released from the substrate by burning off the photoresist film at 575° C. The released multi-layered bodies are then sintered at 800 to 850° C. to produce the multi-layered PZT actuators.

The aforementioned process of using PZT to illustrate the present invention can also be used to produce dense bulk ceramics with nanosized grains by pressureless sintering, thick films with uniform microstructure on different substrates by spin-coating, dip-coating and multi-layered structures by screen-printing or tape-casting. Other specific applications of the present invention may be easily understood by considering the following descriptions of several preferred embodiments.

Example (4)

Yttria Stabilized Zirconia (YSZ) Nanocrystalline Ceramic

Yttria stabilized zirconia for use as a high temperature structural may be produced as followings:
- In a typical recipe of YSZ sol-gel solution, 1 to 2 g of yttrium acetate is dissolved in 4 g of glacial acetic acid. To the resulting solution, a mixture of zirconium propoxide, acetylacetone and MOE with molar ratio of 1:1:4 is added in a Y/Zr molar ratio of 0.03-0.09/1. Then 2 to 3 g of water, 1 g of polyethylene glycol and 1 g glycerol are added to adjust the viscosity.
- Commercial $Y_2O_3$ and $ZrO_2$ powders were mixed with a molar ratio of 3/97 and is dry-milled by high-energy ball milling at 200 rpm for 25-60 hours to get particles with diameters ranging from 8 to 30 nm and cubic phase Then, 2 to 10% surface modifier by weight, preferably a mixture of terpineol and ethyl cellulose, are added and mixed by further ball milling for 5 to 10 hours to produce surface modified nanocrystalline particles. The YSZ sol gel solution obtained previously is than added to the surface modified nanocrystalline particles and further mixed by ball milling at 150 rpm for 15 to 25 hours to form a dispersion or slurry. In a preferred embodiment, 20 to 80 parts by weight, preferably 70 parts by weight, of the surface modified nanocrystalline particles is blended and mixed with 80 to 20 parts by weight, preferably 30 parts by weight, of the sol-gel solution to form a dispersion or slurry.
- Slurries with high solid content thus prepared are extruded to form a powder compact. The powder compacts are calcinated at 500° C. to remove the organic components entirely, followed by cold isostatic pressing at 400-500 MPa to produce green bodies with high density. These green bodies are then sintered at temperatures between 650 to 1,000° C., preferably at 800° C. As the result of this sintering treatment, the YSZ ceramics thus obtained reached relative densities of over 98% of the theoretical and had average grain sizes of below 100 nm.

Example (5)

Thick YSZ Coatings on Metal Structural Parts

For use in high temperature wear and corrosion protection, YSZ ceramic coatings may be deposited on metal structure parts as follows:
- Dispersions or slurries are prepared according to the method of producing YSZ nanocrystalline ceramic above, with preferably 30 parts by weight of the surface modified nanocrystalline particles and 70 parts by weight of said sol-gel solution;
- The slurries are deposited on metal structure parts by either dip-coating, spin-coating or painting multiple layers;
- The parts are sintered at temperatures between 500 to 800° C. to form a dense, uniform polycrystalline ceramic coating on the metal parts.

Example (6)

Porous Bioactive Implant

For biomedical applications, a porous bioactive implant may be produced as following:
- YSZ sol-gel solutions according to Example (4) are prepared as described;
- Commercially-available hydroxyapatite (HAP) and $\beta$-$Ca_3(PO_4)_2$ powders are mixed using high energy ball milling at 200 rpm for 25-60 hours to obtain particles with diameters ranging from 8 to 30 nm.
- The YSZ sol-gel solution obtained is mixed with the nanocrystalline particles by further ball milling at 150 rpm for 15 to 25 hours to form a dispersion or slurry preferably with 40 parts by weight of the nanocrystalline particles to 60 parts by weight of the YSZ sol-gel solution;
- This slurry is then deposited on metal foam or porous ceramic, preferably titanium foam with distributed open pore size of 50 to 400 μm, by dip-coating multiple layers;
- The forms are then sintered between 500 to 800° C. to form a bioactive ceramic coating with nanosized bioactive HAP and $\beta$-$Ca_3(PO_4)_2$ particle embedded in the YSZ matrix. The coating thus formed on porous substrate can be used as an implant to substitute for human bone.

Example (7)

$BaTiO_3$ Multi-Layered Capacitor

A low temperature sintering $BaTiO_3$ (BT) monolithic multi-layered capacitor may be produced as following:
- A BT sol-gel solution is prepared using a procedure similar to that described for the preparation of PZT organometallic solution above, however using barium acetate, acetic acid, MOE and titanium isopropoxide;
- Commercial BT powders is dry milled using high-energy ball milling at 200 rpm for 25-38 hours to get particles with diameters ranging from 8 to 30 nm.
- The BT sol gel solution) is mixed with the BT nanoparticles by further ball milling at 150 rpm for 15 to 25 hours to form a dispersion or slurry preferably with 50 to 70 parts by weight of the nanocrystalline particles and 30 to 50 parts by weight of the BT sol-gel solution;
- An organic vehicle, 10 to 30 parts by weight, is blended with 70-90 parts by weight of the BT sol-gel and other additives to form a slip;
- The slip is then cast into a green sheet with a scapel;
- An Ag/Pd (80/20) electrode layer is then printed on the green sheet;
- Several tens of the green sheets with electrode patterns are aligned and stacked and hot pressed into a laminated bar before being cut into small chips;
- The chips are then sintered between 700 to 1,000° C. for 2 hours after taking special care to perform the binder evaporation at 400 to 500° C.;
- The sintered chips are then polished, external electroded, attached with leadwires and finally coated with waterproof spray.

Example (8)

$Fe_2O_3$—$ZrO_2$ Gas Sensor

For use as gas sensors, such as for oxygen, $Fe_2O_3$—$ZrO_2$ thick film devices are produced as follows:

- A $x\alpha$-$Fe_2O_3$-$(1-x)ZrO_2$ sol-gel solution similar to that described for PZT is prepared using iron acetate, acetic acid, MOE and zirconium propoxide, preferably x=0.2;
- A mixture of zirconia and hematite powders with nominal composition of $x\alpha$-$Fe_2O_3$-$(1-x)ZrO_2$, preferably x=0.2, are mixed using high energy ball milling at 200 rpm for 25-60 hours to get particles with diameters ranging from 8 to 30 nm.
- The sol-gel solution is mixed with the nanocrystalline particles thus obtained by further ball milling at 150 rpm for 15 to 25 hours to form a dispersion or slurry preferably having 50 to 70 parts by weight of the nanocrystalline particles and 30 to 50 parts by weight of the sol-gel solution;
- The dispersion is then blended at 70-90 parts by weight with 10 to 30 parts by weight of organic vehicle and additives to form a paste;
- This paste is then applied onto an alumina substrate with inter-digital Au electrode by screen-printing or spin-coating and then the film and substrate are sintered between 400 to 700° C., preferably at 550° C., for 1 hour. The thick film thus formed has relatively higher strength and durability than that of thick films by conventional methods.

Example (9)

PZT-PMN Nanocrystalline Composite

The method of preparing a PZT nanocrystalline composite as described in Example (1) is followed, however, with $Pb(Nb_{2/3}Mg_{1/3})O_3$ (PMN) powders instead of PZT powders. As a result, a ferro-electric and relaxor ferro-electric nanocrystalline composite may be produced.

Example (10)

$M_{1-x}Zn_xFe_2O_4$-PZT Nanocrystalline Composite

The method of preparing a PZT nanocrystalline composite as described in Example (1) is followed, however, with $M_{1-x}Zn_xFe_2O_4$ (M=Mn, Zn, Ni, Fe, Co) powders, preferably $Mn_{0.6}Zn_{0.4}Fe_2O_4$ powder, instead of PZT powders. As a result, a ferro-electric and ferro-magnetic nanocrystalline composite may be produced.

Example (11)

PLZT Transparent Ceramics

The method of preparing PZT ceramic composite is followed, however, lead lanthanum zirconate titanate (PLZT) powders, preferably with a La/Zr/Ti molar ratio of 7/62/38, and PLZT sol-gel solutions are used instead of PZT powder and sol-gel solution. As a result, transparent PLZT ceramic may be produced by pressureless sintering.

The examples given above will be apparent to one of ordinary skill in the art as significant and novel improvements to the prior art. While we have illustrated the wide-ranging applications of the present invention with specific examples, variations of the invention using other chemicals within the same chemical classes of those described here do not depart from the scope or spirit of the present invention.

We claim:

1. A process for depositing dense, thick piezoelectric composite coatings with uniform microstructure on an electrode layer coated silicon substrate comprising the steps of:

preparing an organo-metallic sol-gel solution of $Pb_{1+y}(Zr_xTi_{1-x})O_3$ (PZT) of desired concentration and chemical formula;

dispersing selected pre-formed nanocrystalline piezoelectric particles with grain sizes less than 100 nm into said sol-gel solution of PZT to form a uniform stable dispersion, slurry or paste, said pre-formed nanocrystalline piezoelectrical particles selected from the group consisting of PZT, PLZT, $Pb(Mg_{1/3}Nb_{2/3})O_3$(PMN), $Pb(Zn_{1/3}Nb_{2/3})O_3$(PZN), $(Ba,Sr)TiO_3$(BST), $PbTiO_3$(PT), $BaTiO_3$(BT), PMN-PT, PZN-PT, and any other composition with good piezoelectric properties;

depositing said stable dispersion, slurry or paste on an electrode layer coated silicon wafer by spin-coating or screen-printing to form a green body; and heating said green body at a temperature from 650° C. up to 800° C.

so as to produce dense, thick piezoelectric composite coating with thickness of between 1 to 100 μm on said silicon substrate, said composite coating possessing grain sizes less than 100 nm and final densities up to 99% of the theoretical limit for such composites.

2. A process according to claim 1 wherein said process further comprises repeating steps a to d to form a multilayered structure, and further comprising photolithography to form a piezoelectric transducer.

3. A process according to claim 2 wherein said piezoelectric transducer comprises a multilayered structure of at least one electrode top layer, at least one patterned piezoelectric composite layer, at least one bottom electrode layer and at least one substrate layer.

4. A process according to claim 2 wherein said piezoelectric transducer with multilayered structure comprises cantilever, bridge and diaphragm structures.

5. The process of claim 2, wherein said piezoelectric transducer transduces ultrasound energy from or to other forms of energy.

6. A process for producing a paste, slip or ink for existing monolithic multilayered device techniques comprising the steps of:

a. providing a selected organo-metallic sol-gel solution, said selected organo-metallic sol-gel solution comprise, in a suitable solvent, metal salt, metal alkoxide and organo-metallic salt of the desired compounds or oxides selected from one or more of PZT, PLZT, $Pb(Mg_{1/3}Nb_{2/3})O_3$(PMN), $Pb(Zn_{1/3}Nb_{2/3})O_3$(PZN), $(Ba,Sr)TiO_3$(BST), $PbTiO_3$(PT), $BaTiO_3$(BT), PMN-PT, PZN-PT, $Bi_2O_3$—ZnO—$Nb_2O_5$(BZN);

b. dispersing selected pre-formed nanocrystalline particles with grain sizes less than 100 nm into said selected organo-metallic sol-gel solution to form a uniform stable mixture, said nanocrystalline piezoelectric particles comprising PZT, PLZT, $Pb(Mg_{1/3}Nb_{2/3})O_3$ (PMN), $Pb(Zn_{1/3}Nb_{2/3})O_3$(PZN), $(Ba,Sr)TiO_3$(BST), $PbTiO_3$(PT), $BaTiO_3$(BT), PMN-PT, PZN-PT, BZN or any other composition with good piezoelectric properties and dielectric properties;

c. further processing said uniform stable mixture to remove all or part of the solvent therein until a desired solid content is reached; and d. blending said processed mixture with an organic vehicle to form said paste, slip or ink.

7. A process further to claim 6, wherein said existing monolithic multilayered device techniques comprise tape-casting, screen-printing and spin-coating.

8. A process further to claim 6, wherein said monolithic multilayered devices comprise multilayered capacitors, multilayered piezoelectric actuator and multilayered piezoelectric transformers.

9. A process further to claim 6, wherein said existing multilayered device techniques further comprise the desirable techniques of:
   low sintering temperature ranging from 750 to 1000° C.; and
   use of cost-effective Ag/Pd electrode paste with Ag/Pd mass ratio from 90/10 to 80/20 as an internal electrode layer.

* * * * *